(12) United States Patent
Hamunen

(10) Patent No.: US 6,770,767 B1
(45) Date of Patent: Aug. 3, 2004

(54) METHOD FOR THE EXTRACTION AND ISOLATION OF NEUTRAL SUBSTANCES FROM A SOAP

(75) Inventor: Antti Hamunen, Raisio (FI)

(73) Assignee: Sterol Techologies Ltd., Raisio (FI)

( * ) Notice: Subject to any disclaimer, the term of this patent is extended or adjusted under 35 U.S.C. 154(b) by 0 days.

(21) Appl. No.: 09/926,396

(22) PCT Filed: Apr. 27, 2000

(86) PCT No.: PCT/IB00/00542

§ 371 (c)(1),
(2), (4) Date: Dec. 11, 2001

(87) PCT Pub. No.: WO00/65004

PCT Pub. Date: Nov. 2, 2000

Related U.S. Application Data

(60) Provisional application No. 60/131,304, filed on Apr. 27, 1999.

(51) Int. Cl.⁷ .................................................. C07J 9/00
(52) U.S. Cl. ...................................................... 552/545
(58) Field of Search ......................................... 552/545

(56) References Cited

U.S. PATENT DOCUMENTS 2,530,810 A * 11/1950 Christenson et al. ...... 260/97.7
3,965,085 A    6/1976 Holmbom et al.

FOREIGN PATENT DOCUMENTS

EP         0122322 A    10/1984
WO      WO 96/10033   *  4/1996

OTHER PUBLICATIONS

Database Caplus 'Online! Chemical Abstracts; & FI 55 679 C (Limotek OY) Sep. 22, 1978.

* cited by examiner

Primary Examiner—Barbara P. Badio
(74) Attorney, Agent, or Firm—Arent Fox PLLC

(57) ABSTRACT

A method for separating neutral substances from a soap containing the neutral substances, the method including the steps of: providing a mixture containing (1) the soap containing the neutral substances, (2) water optionally containing sodium sulfate and (3) a $C_1$–$C_{10}$ hydrocarbon solvent, and heating the mixture to a temperature of at least 140° C., to obtain a soap phase and a hydrocarbon phase containing the neutral substances, the heating step being conducted in a closed system under pressure, wherein the pressure in the system is at least equal to the vapor pressure of the mixture at the temperature used in the heating step; separating the hydrocarbon phase from the soap phase; and optionally separating the neutral substances from the hydrocarbon phase.

51 Claims, No Drawings

METHOD FOR THE EXTRACTION AND ISOLATION OF NEUTRAL SUBSTANCES FROM A SOAP

This application is a 371 of PCT/IB00/00545 filed Apr. 27, 2000 which claims priority under 35 USC § 119(e) of U.S. Provisional Application Serial No. 60/131,304, filed Apr. 27, 1999, which is hereby incorporated by reference.

FIELD OF THE INVENTION

The present invention relates to a method for the separation of useful substances from soaps, such as pulping soap obtained as a by-product in the production of sulfate cellulose or soaps obtained from deodorized distillates of plant oils. More precisely the invention relates to a method for extracting unsaponifiable neutral substances from different kind of soaps. The invention also relates to a method for extracting, separating and purifying sterols from soaps.

BACKGROUND OF THE INVENTION

Soaps contain a lot of alkali salts of fatty and/or resin acids and variable amounts of unsaponifiable neutral substances consisting of e.g. phytosterols, terpene alcohols, fatty alcohols, and aldehydes, ethers, ketones as well as hydrocarbons. Small amounts of fibres, lignins and inorganic salts also exist as impurities in the soap. The amount of neutral substances varies depending on the wood material used for pulping.

Tall oil, made from soaps by acidulation is a valuable raw material for the chemical industry, but generally the neutral substances included in it are not utilized at all. However, from the neutral substances many valuable raw materials can be isolated, such as phytosterols, which can be used e.g. in the food, pharmaceutical and cosmetic industry. Because of the many beneficial characteristics of the phytosterols, the need thereof has grown enormously during the last years. Besides producing hormone preparations by steroid transformations they are used in foodstuffs or medical preparations especially for lowering serum total and LDL cholesterol levels. Most preferable for this kind of use are the stanols and especially the stanol esters, which can be produced e.g. by hydrogenation and esterification of phytosterols.

One method for extracting neutral substances from soaps was proposed in U.S. Pat. No. 2,866,781. In the method proposed therein, esters of a relatively low molecular weight aliphatic acid are used as extraction solvents for aqueous soap solutions. These extraction solvents are, however, not very selective for the neutral substances.

U.S. Pat. No. 3,965,085 discloses a method for refining soaps in which the unsaponifiable neutral substances included in the soap are separated by means of extraction from an aqueous solution containing low molecular weight ketones, such as acetone or methyl ethyl ketone, using as the water-immiscible solvent an aliphatic, aromatic, alicyclic or halogenated hydrocarbon. In the Examples of this patent, extraction is conducted at temperatures below 75° C. The added ketone is essential in the disclosed extraction method, since it prevents the formation of emulsions in the soap solution and thereby facilitates the extraction process.

U.S. Pat. No. 2,530,809 discloses the extraction of neutral substances from tall oil soaps using a mixture of the soaps with a lower alcohol and water. Suggested as solvents for the unsaponifiable material are alkanes or other petroleum fractions, ethers, aromatic hydrocarbons or chlorinated hydrocarbons. The extraction procedure is conducted at temperatures of between 80 and 120° F. (which is between about 27 and 49° C.). In this case, the lower alcohol acts as an emulsion breaker.

Problems with the two extraction methods described in U.S. Pat. No. 3,965,085 and U.S. Pat. No. 2,530,809 are particularly focused on their use of a two-component solvent system, which involves difficult solvent regeneration systems in large scale production. Complete removal of the alcohol (U.S. Pat. No. '809) or the ketone (U.S. Pat. No. '085) from the soap solution is also technically impossible, because of foaming problems. The remaining solvent is also to some extent harmful for further processing of the soap. If present, it causes problems e.g. in the distillation of crude tall oil. But, above all, the inevitable solvent losses in these methods make them not very economic and these methods do not take into account environmental aspects.

FI 55 679 discloses an extraction method wherein a long chain $C_{12}$–$C_{35}$ hydrocarbon in combination with water is used for extracting neutral substances from soap. This method suffers from the drawbacks involved in using long chain hydrocarbons, which need very high temperatures for regeneration and therefore are not particularly suitable in large scale production. Another problem involved with this method is that the long chain hydrocarbons and the light fractions of the neutral substances have boiling points close to each other, and the recirculation of this solvent may therefore lead to higher amounts of light fractions of the neutral substances in the process system.

All the prior disclosed methods for extracting neutral substances from soaps have some technical problems, which have been solved by the methods according to the present invention.

SUMMARY OF THE INVENTION

It has now surprisingly been realized that neutral substances can be extracted from different kind of soaps by the use of a short chain ($C_1$–$C_{10}$) hydrocarbon solvent and an aqueous solution of the soaps. This allows the best regeneration system for the solvent, and the problems associated with the use of long chain hydrocarbons are avoided. No other organic solvent is needed in the method of the invention because, instead of using additives such as alcohols or ketones as in the art, emulsion breaking can be accomplished by increasing the temperature of the mixture to at least 140° C., and thereby the phase separation needed for the extraction to proceed is accomplished.

In a first aspect of the present invention there is provided a method for the separation of neutral substances from soaps comprising the steps of:

extracting neutral substances into a hydrocarbon phase by mixing the soap with water optionally containing sodium sulfate, and with a short chain hydrocarbon solvent at ambient or elevated temperature, and raising the temperature of the mixture to at least 140° C., to obtain a hydrocarbon phase containing neutral substances, and a soap phase, the extraction step being conducted in a closed system, wherein the pressure in the system is at least equal to the vapor pressure of the extraction mixture at the temperature used for extraction, separating the hydrocarbon phase containing neutral substances from the soap phase, and optionally separating the neutral substances from the hydrocarbon phase.

In a second aspect of the present invention there is provided a method for the separation of sterols from soaps comprising the steps of:

extracting neutral substances into a hydrocarbon phase by mixing the soap with water optionally containing sodium sulfate, and with a short chain ($C_1$–$C_{10}$) hydrocarbon solvent at ambient or elevated temperature, and raising the temperature of the mixture to at least 140° C., to obtain a hydrocarbon phase containing neutral substances, and a soap phase, the extraction step being conducted in a closed system, wherein the pressure in the system is at least equal to the vapor pressure of the extraction mixture at the temperature used for extraction, separating the hydrocarbon phase containing neutral substances from the soap phase, optionally separating the neutral substances from the hydrocarbon phase, separating sterols from the hydrocarbon phase containing neutral substances or from the neutral substances, and optionally purifying the sterols.

The above steps (a) to (c) can be carried out as explained above for the first aspect of the present invention.

DESCRIPTION OF THE PREFERRED EMBODIMENTS

A preferred method for separating neutral substances from a soap containing the neutral substances comprises the steps of:

(a) providing a mixture comprising (1) the soap containing the neutral substances, (2) water optionally containing sodium sulfate and (3) a $C_1$–$C_{10}$ hydrocarbon solvent, and heating the mixture to a temperature of at least 140° C., to obtain a soap phase and a hydrocarbon phase containing the neutral substances, the heating step being conducted in a closed system under pressure, wherein the pressure in the system is at least equal to the vapor pressure of the mixture at the temperature used in the heating step:

(b) separating the hydrocarbon phase from the soap phase; and (c) optionally separating the neutral substances from the hydrocarbon phase.

A preferred method for purifying sterols from a soap containing the sterols comprises the steps of:

(a) providing a mixture comprising (1) the soap containing the sterols, (2) water optionally containing sodium sulfate and (3) a $C_1$–$C_{10}$ hydrocarbon solvent, and heating the mixture to a temperature of at least 140° C., to obtain a soap phase and a hydrocarbon phase containing the sterols, the beating step being conducted in a closed system under pressure, wherein the pressure in the system is at least equal to the vapor pressure of the mixture at the temperature used in the heating step;

(b) separating the hydrocarbon phase and the soap phase; and (c) purifying the sterols from the hydrocarbon phase.

Preferable soaps useable as starting material in the methods of the invention are e.g. crude soaps isolated from black liquor in the sulfate cellulose production process or saponified tall oil pitch (pitch soaps) arrived at after removing e.g. by distilling tall oil from pulping soap and saponifying the remaining tall oil pitch. The use of pitch soap is especially preferable, if sterols are to be isolated from the neutral substances (unsaponifiables or neutrals), because the sterol content is very high in this process flow, i.e. about 8 to 20 weight-% of the pitch dry weight.

The term "short chain hydrocarbon" includes hydrocarbons containing 1–10 carbon atoms, more preferably 5–8 carbon atoms. Preferred short chain hydrocarbon solvents in the methods are straight chain hydrocarbons (preferably pentane, hexane, heptane or octane), branched chain hydrocarbons, hydrocarbons containing cycloaliphatic structures like cyclohexane or methylcyclohexane or hydrocarbon mixtures comprising any of these compounds. Most preferred extraction solvents are hexane and/or heptane.

The temperature of the extracting step is preferably between 140° C. and 190° C. The extraction process can technically also be performed at higher temperatures, but it is then less economic. More preferably, the temperature is between 150 and 185° C. and most preferably between 165 and 185° C.

The length of time the temperature needs to be raised to accomplish the desired result is not important. It should be at least the time needed to establish the needed contact between the hydrocarbon phase and the soap phase. The time therefore depends on the degree of mixing. In most cases, the length of time may be several seconds only.

The pressure in the extraction step depends on the temperature; the higher the temperature, the higher the pressure. Preferably the pressure is equal to the vapor pressure at the temperature of the extraction mixture in the extraction step.

In the methods of the invention, sodium sulfate may optionally be added, e.g. dissolved in the water added to the soap. Also the soap itself often contains sodium sulfate. This salt is known to enhance the extraction of the neutral substances.

The amount of solvents useable in the methods may vary largely. However, the typical ratio of soap (in dry weight) to water (by weight) to hydrocarbon solvent (by weight) is 1:>1:>1. The amounts used in the methods according to the invention are preferably such that the amount of water added is minimized, thereby avoiding the problem of handling large amounts of waste water and minimizing the costs of the extraction process. Instead, more hydrocarbon may be used to make the extraction more effective. The hydrocarbon is easily separated and recirculated e.g. in a closed system. The water, on the other hand, typically has to be evaporated from the soap and recirculated or purified and let into the waste water.

It has been found that using water in amounts higher than 3 times the amount of dry soap does not enhance the extraction of the neutral substances. A method using an elevated amount of hydrocarbon solvent is more energy sparing than a method in which a large amount of water has to be separated from the soap. Therefore, the extraction process of the invention preferably may be realized by using 1–3 times as much water as the amount of soap, most preferably 2–3 times. The amount of hydrocarbon is preferably 2–6 times the amount of dry soap, more preferably 3–6 times, most preferably 4–5 times. At these ratios a very effective extraction can be accomplished. Preferably, the weight ratios of the soap to water to hydrocarbon is 1:1–3:2–6, more preferably 1:2–3:3–6, most preferably 1:2–3:4–5, to obtain a high yield of neutral substances. The extraction yield is better the more solvents are used, but the use of larger amounts of solvents leads to less economic processing of the applied solvents.

The hydrocarbon phase separated during the extraction may contain small residues of fatty and resin acid salts and inorganic salts as well. These components may be harmful impurities when separating valuable components, to such as sterols, from the neutral fraction. It is possible to wash these impurities from the hydrocarbon phase with water. It has been noticed that the washing procedure has improved results if performed at elevated temperatures and pressure, i.e. at more or less similar conditions as the extraction has been a performed, if there is any tendency that the soap residues emulsify the washing water into the hydrocarbon phase and it would thereby be impossible to get the water phase separated from the hydrocarbon phase. The water wash can suitably be performed at temperatures above 80° C., most preferably above about 130° C., in a closed system. Normally, the water wash cannot be performed in open reactor systems, because the solvents evaporate too quickly to make the process efficient.

This high pressure water wash can be accomplished as a batch process or more preferably continuously using e.g. a countercurrent column or mixer-settler extraction equipment.

The separated hydrocarbon phase can be reduced by partial evaporation, and this partly evaporated hydrocarbon phase can be washed with water as explained above.

Neutral substances can be separated from the hydrocarbon phase by evaporating the same to dryness.

Neutral substances can be used for isolation of e.g. sterols, wax alcohols and/or squalene (from birch based soap). When the aim is to isolate sterols from soaps, the disclosed extraction method can be followed by one or more separation and optionally performed purification steps in order to further purify the sterols from any other neutral substances.

Thus, in the second aspect of the present invention, sterols are separated from the hydrocarbon phase containing neutral substances or from the neutral substances themselves, and optionally purified to remove any other components (e.g. impurities) in a final cleaning stage.

Some preferred ways to separate and purify the sterols are explained in the following disclosure.

From the hydrocarbon phase, or preferably from the water washed hydrocarbon phase, the sterol components may be crystallized. This may be done simply by cooling the hydrocarbon phase to a suitable temperature, e.g. to about 25° C. or less, followed by filtration or using some other solids/liquid separation process. Preferably the obtained sterol crystals are washed with fresh hydrocarbon. The procedure may optionally be realized by evaporating some of the hydrocarbon, optionally washing this reduced hydrocarbon phase with water, and performing the crystallization procedures from this phase. Also in this case it is preferred to wash the obtained crystals with fresh hydrocarbon. However, it has been noticed that this crystallization procedure is not optimal, because some impurities (which typically cannot be analyzed by standard gas chromatographic methods and are therefore often called "non-elutables") tend to co-crystallize with the sterols. In addition to this, the crystal forms of sterols crystallized from hydrocarbon are usually flat, soft plates which tend to be stuck together during filtration. This usually makes the crystal separation procedures difficult.

Therefore, if small amounts of a lower ($C_1$–$C_6$) alkanol, especially methanol, are added to the hydrocarbon solution containing the sterols and optionally other neutral substances, better crystals are obtained. Advantageously the conditions for such a crystallization procedure may be: 1 part sterols/neutral substances, 1.5–5 parts hydrocarbon and 0.03–0.5 part alkanol, and an even more preferred composition comprises 1 part sterols/neutral substances, 1.5–3.5 parts hydrocarbon and 0.03–0.35 parts alkanol. In order to increase the sterol yield it may be advantageous to also add water to the crystallization mixture. The preferred amount may vary from 0 to 1 part water per 1 part sterols/neutral substances.

If further purification of the obtained sterols is needed, this may be accomplished by recrystallization, which preferably may be performed with e.g. a similar solvent composition as used in the first crystallization, or more preferably from a lower alkanol (preferably methanol) rich solvent.

Advantageously the composition of the recrystallization solution may be 1 part sterols/neutral substances, 1–3 parts hydrocarbon and 1–15 parts alkanol.

The obtained sterol crystals from the crystallization or recrystallization are preferably washed. This can be performed using any suitable solvent. Usually it is preferred to use the same solvent or mixture of solvents that are used in the isolation process, which solvents therefore already are available at the facility. Preferably the same solvent composition as used in the crystallization or recrystallization is used.

All the crystallization and/or recrystallization procedures are performed by standard methods, i.e. by heating the mixture to dissolve the sterols, if the mixture is not hot already from the preceding process steps, and then allowing the mixture to cool to crystallize the sterols. The crystals may be isolated by e.g. filtration or centrifuigation.

To minimize the loss of sterols into the solvents used in the recrystallization, the used solvent is preferably evaporated to dryness or to a reduced solution, which preferably is recirculated to the first crystallization procedure for a following batch or in a continuous process.

Especially in the case of black liquor soap neutral substances, an alternative approach in separating the sterols is to use a lower alkanol (preferably methanol) rich solvent in the first crystallization step. This procedure has proven to give very pure sterols in one step, and a further advantage is the excellent filterability of the sterols. The weight composition of the crystallization mixture in this case may be: 1 part sterols/neutral substances, 1.5–4 parts alkanol, 0.01–1.0 parts hydrocarbon and 0–0.05 parts water, preferably 1 part sterols/neutral substances, 1.5–4 parts alkanol, 0.01–0.3 parts hydrocarbon and 0–0.02 parts water, and most preferably 1:2.5:0.1:0–0.0015. In this procedure, the washing of the crystallized sterols is preferably performed with a non-polar solvent (e.g. a hydrocarbon), because the impurities stuck to the surface of the crystals are not as soluble in a polar solvent.

If the hydrocarbon phase obtained from the extraction process as such or washed with water is dried by evaporating the solvent, any known method for separating the sterols from neutral substances and optionally purifying them to remove impurities may be used. A very preferred solvent mixture for crystallizing the sterols comprises methyl ethyl ketone (MEK), a lower alkanol (preferably methanol) and water. A preferred composition comprises, by weight, 50–80 parts MEK, 5–40 parts alkanol and 2–20 parts water. A more preferred composition comprises 60–70 parts MEK, 20–35 parts alkanol and 5–10 parts water. The sum of these parts is preferably 100. A typical composition comprises about 70 parts MEK, about 20 parts alkanol and about 10 parts water.

The amount of MEK in the composition is preferably at most 80% by weight, more preferably at most 75% by weight. The amount of lower alkanol is preferably at least 14% by weight, more preferably at least 17% by weight, and the amount of water is preferably at least 6% by weight, more preferably at least 8% by weight.

The following examples illustrate the invention in more detail. All the percentages given in the examples are calculated as weight—%.

EXAMPLE 1

Soap originated from *Pinus radiata* pine wood pulp was extracted in a closed reactor as batch extraction. The soap contained 15% unsaponifiables calculated from the soap solids and the unsaponifiables contained 35% sterols. 500 g soap (solids content 60%) was mixed with 400 g water and 900 g hydrocarbon solvent LIAV110 (a mixture of straight chain, branched chain and cycloaliphatic saturated hydrocarbons, mainly $C_6$–$C_8$ hydrocarbons, from Neste Oy) and the temperature was elevated to 150° C. After 5 min mixing (300 rpm), the phases were allowed to separate for a few minutes. The lower phase was drained out slowly from the bottom valve through a Liebig type water cooled bomb. No clear intermediate ("rag") layer was detected between the lower soap layer and upper hydrocarbon layer. When evaporated to dryness, 36 (yield 80%) unsaponifiables was recovered from the hydrocarbon layer. It contained 12.3 g sterols, which was 78% of the sterols in the feed soap.

EXAMPLE 2

The extraction procedure of example 1 was performed using pure heptane as a solvent. No emulsion formation was noticed. The recovery of the unsaponifiables was 78% (recovery of sterols 77%).

EXAMPLE 3

Saponified pitch, mainly originated from tall oil of *Pinus taedapine* wood pulping, was used as the material to be extracted. The solids content was 65%, the amount of unsaponifiables 31% and the amount of sterols 36% of the unsaponifiables. The extraction was performed as a single stage batch extraction as disclosed in example 1. The extraction solvent was LIAV110 and the ratios of dry pitch soap 1.0, total water 2.0 and solvent 3.9 parts. The extraction temperature was 168° C. No clear middle layer was observed. The recovery of the unsaponifiables and the sterols into the hydrocarbon phase was 79 and 75%, respectively.

EXAMPLE 4

The same kind of soap used as raw material in example 1 was extracted continuously and countercurrently in a two-stage mixer-settler type extraction equipment. Soap, water and solvent (LIAV110) were mixed in static mixers and settling of the phases took place in settling tanks. Solvent feed was 384 kg/h, additional water feed 150 kg/h, and soap feed 131 kg/h. The temperature in both settlers was 178° C. and the pressure in the first decanter was 19.2 bars, and in the second, 18.7 bars. In the interphase between the soap and the hydrocarbon layers only a small middle layer was observed. The recovery of the unsaponifiables into hydrocarbon in this two-stage extraction was 96% and the recovery of sterols was 94%.

EXAMPLE 5

Pitch soap (*Pinus taeda* based, unsaponifiables 29.6%, sterols 41% of the unsaponiflables) was extracted with the commercial hydrocarbon mixture LIAV110 in a two-stage mixer-settler extraction equipment (the same as in example 4). The feed ratios of dry soap to water to hydrocarbon solvent were 1:2.4:4.7 and the total feed rate was 730 kg/h. The temperatures in the settler vessels were 182° C. and 184° C. and the pressures were 20.7 and 20 bars, respectively. No interfering interphase layer was observed during the extraction. The recoveries of unsaponifiables and sterols into the hydrocarbon phase were 95.8% and 97%, respectively.

EXAMPLE 6

The extraction procedure disclosed in example 5 was performed using the feed ratios 1:1.3:6.4. The total feed rate was 570 kg/h, and the temperatures and pressures were 178° C. and 19.3 bars, and 182° C. and 18.9 bars, respectively. The yield of unsaponifiables and sterols into the hydrocarbon phase was 97.4 and 97.9%, respectively.

EXAMPLE 7

The starting material in this process was the unsaponifiables separated from tall oil pitch (100% pine origin). The pitch was first saponified at 170° C. with NaOH, and then the unsaponifiables were extracted using a hydrocarbon solvent as in example 5 at the saponification temperature and prevailing vapor pressure in the system.

EXAMPLE 8

The hydrocarbon phase (solids content 11.3%) from example 5 was washed with water as a continuous extraction process in a one-stage mixer-settler equipment. The feed rate of the hydrocarbon phase was 320 kg/h and the feed rate of the water was 100 kg/h. The temperature was 160° C. The ash content of the solids in the dried neutrals before the wash was 0.3%, and after wash, 0.04%. According to FTIR analyses the substance transferred to the water phase consisted mainly of carboxylic acid salts.

EXAMPLE 9

The hydrocarbon phase from example 8 was cooled to 20° C., and the precipitated sterols were filtered and washed with fresh hydrocarbon solvent. When 100 g of dry neutrals was used as starting material, 22.5 g of a sterol blend consisting of sitosterol, sitostanol, campesterol and campestanol and nonelutable impurities was obtained. The sterol content was 80%.

EXAMPLE 10

10 g sterols (80%) from example 9 were dissolved in a solvent consisting of 20 g LIAV110 and 90 g methanol by refluxing. The sterols were recrystallized by cooling, separated by filtration and washed with fresh recrystallization solvent. The amount of crystallized product was 6.9 g of 97% pure sterols.

EXAMPLE 11

The hydrocarbon phase of example 8 was evaporated to a concentration where the neutrals/LIAV110 ratio was 1:2.5. 0.05 parts of MeOH was added calculated on the amount of neutrals and the blend was refluxed resulting in a clear solution. After cooling to 25° C. under gentle magnetic stirring, the formed crystals were filtered and washed with crystallization solvent (LIAV:MeOH 2.5:0.05). The sterol yield was 67.3% of the sterol content in the neutrals and the purity was 96.5%.

EXAMPLE 12

The hydrocarbon phase of example 8 was evaporated to a concentration where the neutrals/LIAV110 ratio was 1:3.2. 0.35 parts of MeOH calculated on the amount of neutrals in the hydrocarbon phase and 1 part of water was added, and the mixture was refluxed to yield a clear solution. After crystallization, filtration and washing with a solvent of the same composition as the crystallization solvent, 73.4% of a 95.5% pure sterol blend was obtained.

EXAMPLE 13

The starting material was the hydrocarbon extract from example 4 that contains unsaponifiables. The solvent was evaporated so that the neutrals:LIAV ratio was 1:0.1. 2.5 parts of methanol was added, calculated from the amount of neutrals, and the mixture was refluxed. The crystallization was accomplished by cooling to about 25° C., the crystals were filtered and washed with pure LIAV110. The dried product was a 97.5% pure sterol blend. The sterol recovery was 63.5% of the original sterol content in the hydrocarbon extract used as feed solution.

EXAMPLE 14

The same procedure as described in example 13 was performed. The difference in this case was that the methanol used contained 1.5% water. The sterol purity was 95.8% and the yield 74.99% of the original sterol content in the hydrocarbon phase.

EXAMPLE 15

The extraction solvent was distilled off from the hydrocarbon phase obtained in example 7. Then the fraction of unsaponifiables (35% sterols) was dissolved by refluxing into a solvent mixture consisting of 65% MEK, 30% MeOH and 5% water (10 g unsaponifiables/80 g solvent). Crystallization of the sterols took place when the mixture was allowed to cool to 25° C. for 1.5 h by gentle mixing with a magnetic stirrer. The crystals were filtered and washed with fresh crystallization solvent. 2.8 g of 96.5% pure dry sterol was obtained.

What is claimed is:

1. A method for separating neutral substances from a soap containing the neutral substances, the method comprising the steps of:
   (a) providing a mixture comprising (1) the soap containing the neutral substances, (2) water optionally containing sodium sulfate and (3) a $C_1$–$C_{10}$ hydrocarbon solvent, and heating the mixture to a temperature of at least 140° C., to obtain a soap phase and a hydrocarbon phase containing the neutral substances, the heating step being conducted in a closed system under pressure, wherein the pressure in the system is at least equal to the vapor pressure of the mixture at the temperature used in the heating step and wherein no alcohol or ketone is used in step (a);
   (b) separating the hydrocarbon phase from the soap phase; and
   (c) optionally separating the neutral substances from the hydrocarbon phase.

2. The method of claim 1, wherein the hydrocarbon solvent is selected from the group consisting of hexane, heptane, octane, cyclohexane, methylcyclohexane and mixtures thereof.

3. The method of claim 1, wherein the temperature is between 140° C. and 190° C.

4. The method of claim 3, wherein the temperature is between 165° C. and 185° C.

5. The method of claim 1, wherein the soap, the water and the hydrocarbon solvent are provided in the mixture in a weight ratio of 1:>1:>1, based on the dry weight of the soap.

6. The method of claim 5, wherein the weight ratio is 1:>1–3:2–6.

7. The method of claim 5, wherein the weight ratio is 1:2–3:3–6.

8. The method of claim 5, wherein the weight ratio is 1:2–3:4–5.

9. The method of claim 1, comprising the further step of reducing the separated hydrocarbon phase produced in step (b) by evaporation.

10. The method of claim 1, comprising the further step of washing the separated hydrocarbon phase produced in step (b) with water.

11. The method of claim 9, comprising the further step of washing the reduced hydrocarbon phase produced in said further step with water.

12. The method of claim 10, wherein said washing step is performed at a temperature of at least 80° C. under pressure.

13. The method of claim 11, wherein said washing step is performed at a temperature of at least 80° C. under pressure.

14. The method of claim 12, wherein the temperature is at least 130° C.

15. The method of claim 13, wherein the temperature is at least 130° C.

16. The method of claim 1, wherein said separating step (c) comprises evaporating the hydrocarbon phase to dryness.

17. The method of claim 1, wherein the neutral substances are selected from the group consisting of sterols, terpene alcohols and fatty alcohols.

18. A method for purifying sterols from a soap containing the sterols, the method comprising the steps of:
   (a) providing a mixture comprising (1) the soap containing the sterols, (2) water optionally containing sodium sulfate and (3) a $C_1$–$C_{10}$ hydrocarbon solvent, and heating the mixture to a temperature of at least 140° C., to obtain a soap phase and a hydrocarbon phase containing the sterols, the heating step being conducted in a closed system under pressure, wherein the pressure in the system is at least equal to the vapor pressure of the mixture at the temperature used in the heating step and wherein no alcohol or ketone is used in step (a);
   (b) separating the hydrocarbon phase and the soap phase; and
   (c) purifying the sterols from the hydrocarbon phase.

19. The method of claim 18, wherein the hydrocarbon solvent is selected from the group consisting of hexane, heptane, octane, cyclohexane, methylcyclohexane and mixtures thereof.

20. The method of claim 18, wherein the temperature is between 140° C. and 190° C.

21. The method of claim 20, wherein the temperature is between 165° C. and 185° C.

22. The method of claim 18, wherein the soap, the water and the hydrocarbon solvent are provided in the mixture in a weight ratio of 1:>1:>1, based on the dry weight of the soap.

23. The method of claim 22, wherein the weight ratio is 1:>1–3:2–6.

24. The method of claim 22, wherein the weight ratio is 1:2–3:3–6.

25. The method of claim 22, wherein the weight ratio is 1:2–3:4–5.

26. The method of claim 18, comprising the further step of reducing the separated hydrocarbon phase produced in step (b) by evaporation.

27. The method of claim 18, comprising the further step of washing the separated hydrocarbon phase produced in step (b) with water.

28. The method of claim 26, comprising the further step of washing the reduced hydrocarbon phase produced in said further step with water.

29. The method of claim 27, wherein said washing step is performed at a temperature of at least 80° C. under pressure.

30. The method of claim 28, wherein said washing step is performed at a temperature of at least 80° C. under pressure.

31. The method of claim 29, wherein the temperature is at least 130° C.

32. The method of claim 30, wherein the temperature is at least 130° C.

33. The method of claim 18, wherein said purifying step (c) comprises evaporating the hydrocarbon phase to dryness.

34. The method of claim 18, wherein the hydrocarbon phase additionally contains other neutral substances from the soap, and step (c) further comprises purifying the sterols from the other neutral substances by dissolving the other neutral substances in a solvent mixture comprising methyl ethyl ketone, a $C_1$–$C_6$ alkanol and water, and thereafter crystallizing the sterols from the solvent mixture.

35. The method of claim 34, wherein the methyl ethyl ketone, the $C_1$–$C_6$ alkanol and the water are present in the solvent mixture in a weight ratio of 50–80:5–40:2–20.

36. The method of claim 35, wherein the weight ratio is 60–70:20–35:5–10.

37. The method of claim 34, comprising the further step of washing the sterol crystals with a solvent.

38. The method of claim 37, wherein the solvent is a mixture comprising methyl ethyl ketone, a $C_1$–$C_6$ alkanol and water.

39. The method of claim 18, wherein step (c) comprises crystallizing the sterols from the hydrocarbon phase by cooling the hydrocarbon phase and thereafter separating the formed crystals from the hydrocarbon phase.

40. The method claim 39, comprising the further step of washing the crystals and/or recrystallizing the sterols.

41. The method of claim 40, wherein the sterols are recrystallized in a solvent mixture comprising a hydrocarbon and a $C_1$–$C_6$ alkanol.

42. The method of claim 41, wherein the sterols, the hydrocarbon and the $C_1$–$C_6$ alkanol are present in the solvent mixture in a weight ratio of 1:1–3:1–15.

43. The method of claim 18, wherein step (c) comprises reducing the hydrocarbon phase by evaporation, mixing the reduced hydrocarbon phase with a $C_1$–$C_6$ alkanol and optionally water, and crystallizing the sterols from the mixture.

44. The method of claim 43, wherein the sterols, the $C_1$–$C_6$ alkanol, the hydrocarbon and the water are present in a weight ratio of 1:1.5–4:0.01–1.0:0–0.05, based on the dry weight of the sterols.

45. The method of claim 44, wherein the weight ratio is 1:1.5–4:0.01–0.3:0–0.02.

46. The method of claim 34, wherein the $C_1$–$C_6$ alkanol is methanol.

47. The method of claim 43, wherein the $C_1$–$C_6$ alkanol is methanol.

48. The method of claim 1, wherein the temperature is at least 150° C.

49. The method of claim 1, wherein the temperature is between 150° C. and 185° C.

50. The method of claim 18, wherein the temperature is at least 150° C.

51. The method of claim 18, wherein the temperature is between 150° C. and 185° C.

* * * * *